United States Patent [19]

Moller et al.

[11] 4,036,891

[45] July 19, 1977

[54] PROCESS FOR PREPARING PARAFORMALDEHYDE

[76] Inventors: Jens C. T. Moller, 5245 Hayledge Court, Columbia, Md. 21045; Ove E. Hansen, Skovgards Alle 261, 3500 Ll. Vaerlose, Denmark

[21] Appl. No.: 644,944

[22] Filed: Dec. 29, 1975

[51] Int. Cl.² .............................................. C07C 47/10
[52] U.S. Cl. ................................................... 260/615.5
[58] Field of Search ...................................... 260/615.5

[56] References Cited

U.S. PATENT DOCUMENTS

| | | | |
|---|---|---|---|
| 3,316,309 | 6/1967 | Mann et al. | 260/615.5 |
| 3,595,926 | 7/1971 | Mann et al. | 260/615.5 |
| 3,772,392 | 11/1973 | Paleologo et al. | 260/615.5 |

*Primary Examiner*—Howard T. Mars
*Attorney, Agent, or Firm*—Schuyler, Birch, Swindler, McKie & Beckett

[57] ABSTRACT

A process for the preparation of paraformaldehyde in which concentrated formaldehyde solution is formed into powdery paraformaldehyde by spraying the solution into a spray cooling and drying chamber and contacting the sprayed solution with a stream of inert gas such as nitrogen or air having a temperature of about 30°–40° C. The particulate product, which may be slightly sticky and agglomerated, is transferred from the spray cooling tower to a multistage fluidized bed each stage of which is fluidized with air of temperature higher than that of the preceding stage. Inert gas used to fluidize the particles enters the first stage, which is preferably a vibratory fluidized bed, at a temperature in the range 45–70° C. Particles in the first stage are simultaneously cured, dried, and concentrated to preferably about 90–91% formaldehyde concentration. The concentrated powder from the first stage is transferred to a second fluidized stage having the fluidized gas entering the bed at a temperature in the range 70–100° C. The resultant product is further concentrated to a formaldehyde concentration of preferably about 95%. The final product is particulate in form, nonsticky, free-flowing, and has little or no dust.

8 Claims, 1 Drawing Figure

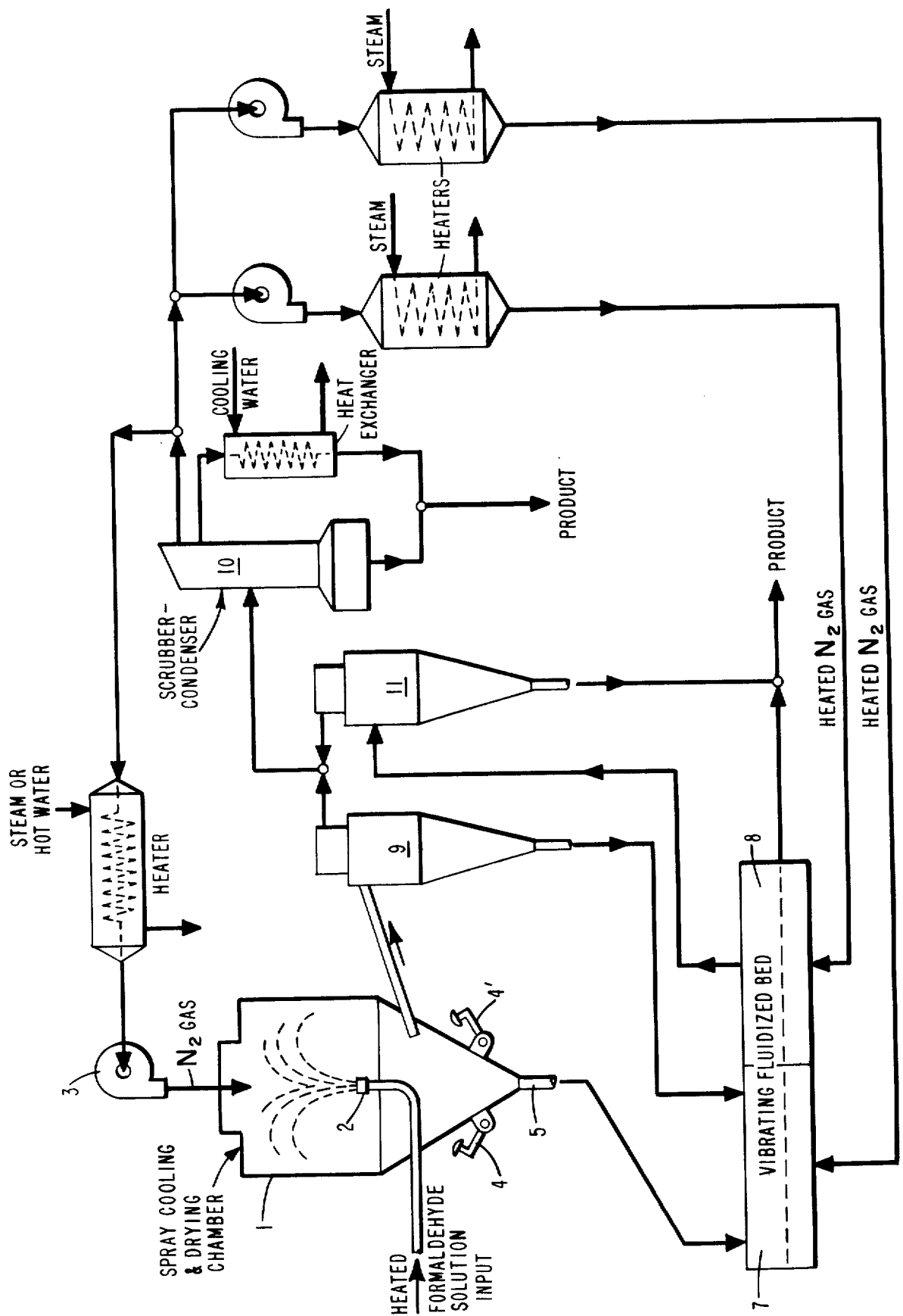

PROCESS FOR PREPARING PARAFORMALDEHYDE

BACKGROUND OF THE INVENTION

1. Field of the Invention

The invention described and claimed herein relates to the preparation of powdery paraformaldehyde from a concentrated solution of formaldehyde.

2. Description of the Prior Art

Formaldehyde is a large volume chemical with a wide variety of industrial uses. Much formaldehyde is sold and used as a water solution. However, during recent years an increasing amount has been sold in solid form as paraformaldehyde.

Paraformaldehyde is a mixture of polymers of formaldehyde of different molecular weight. Paraformaldehyde is usually made by concentration of a formaldehyde solution and solidification of the concentrated solution by cooling. Paraformaldehyde is available as powder, flakes, or prills, and in this form is generally storage stable, convenient to transport and readily soluble in water or alcohol, in which the paraformaldehyde readily depolymerizes to form solutions of formaldehyde.

It is known that a free-flowing paraformaldehyde product can be produced by spraying an aqueous formaldehyde concentrate containing 80-90 weight percent of formaldehyde downwardly into a spray cooling chamber while passing a current of air having a temperature between 40° and 60° C. upwardly through the cooling chamber. The chamber is so constructed as to maintain a fluidized bed of the sprayed particulate product in the lower portion thereof until dry, nonsticky particulate paraformaldehyde is formed. Such a process is described in Mann et al. U.S. Pat No. 3,316,309 and, while said to be operative on a small scale, has been criticized in a later Mann et al. patent as not satisfactory for large scale technical operations since the small paraformaldehyde spheres which are the primary product are not sufficiently free of tackiness and quickly agglomerate causing the process to come to a standstill because of complete clogging of the nozzles employed, the spray chamber, the drying air passages and particularly the sieve grates through which air is supplied to the fluidized bed maintained in the lower portion of the spray dryer.

An attempt to solve the problems of the aforementioned process is described in Mann et al. U.S. Pat. No. 3,595,926, which discloses and claims a process for preparing paraformaldehyde in which an aqueous formaldehyde concentrate containing 80-90 weight percent of formaldehyde is sprayed downwardly into a spray cooler constructed so as to maintain a fluidized bed of the sprayed particulate product in the lower portion of the cooler. It is a critical aspect of this latter process that the temperature of the cooling gas in the cooling chamber be quite cool, preferably between −40° C. and +30° C. and that the paraformaldehyde spheres remain in the fluidized bed of the cooling tower until they have been cooled to a temperature below 40° C., preferably 20°-30° C. in order to avoid stickiness. The cooled pellets are then dried in a contact dryer to a final formaldehyde content of 92-97%. Needless to say, a process which requires considerable cooling of the product may in many climates necessitate the purchase of special refrigeration equipment thereby raising the overall cost and complexity of the process.

In U.S. Pat. No. 3,772,392 there is shown a process for preparation of paraformaldehyde by spraying concentrated formaldehyde solution into a spray cooler and subsequently curing the product. A polymerization catalyst or a regulator is required to regulate curing of the product which occurs on a band conveyor prior to any drying of the paraformaldehyde. The cured product is transferred to a hot air dryer or a fluidized bed for subsequent drying and concentration.

It would be highly desirable that a spray cooling process for producing paraformaldehyde be capable of functioning without the use of polymerization catalyst or regulator. It would be further desirable that a spray cooling process for producing paraformaldehyde be capable of functioning without the necessity of maintaining a fluidized bed in the bottom of the spray cooling tower. It is still further desirable that a spray cooling process for producing paraformaldehyde permit the removal of a powdery product from the spray cooling tower in a somewhat sticky or agglomerated condition at temperatures above 40° C.

BRIEF SUMMARY OF THE INVENTION

It is an object of this invention to produce a free-flowing paraformaldehyde powder which is substantially free of dust.

It is a further object of this invention to prepare paraformaldehyde of high concentration in powder form without the necessity of using refrigeration equipment to cool the fluidizing air and without the necessity of using catalysts or polymerization regulators.

It is a further object of this invention to produce paraformaldehyde by concentrating a solution of paraformaldehyde in a spray cooler-dryer to form a particulate product which may be slightly sticky and removing the product from the spray chamber at temperatures which may be above 40° C. for subsequent simultaneous curing, drying, and concentration in a fluidized bed, preferably a vibrating fluidized bed.

It is yet another object of this invention to simultaneously dry and cure a paraformaldehyde product which may be slightly sticky without the necessity of a catalyst by continuously passing said product through a plurality of fluidized beds each of which has fluidizing gas entering the bed at a temperature higher than that of the next preceding bed, the first fluidized bed preferably being a vibrating bed and the fluidizing gas of the first bed being below the sticking point of the product preferably at a temperature in the range 45°-70° C.

These and other objects of the invention are achieved by a process for the production of a powdery, free-flowing paraformaldehyde comprising:

a. forming a particulate formaldehyde product by spraying a concentrated aqueous formaldehyde solution containing from about 75 to about 90% formaldehyde by weight into a spray chamber and contacting the formaldehyde spray with an inert cooling and drying gas flowing through said chamber, b. removing said particulate product from said spray chamber and passing said product into a vibrating fluidized bed, and c. simultaneously drying, curing, and concentrating said product in said vibrating fluidized bed by fluidizing said product with an inert gas, said gas being at a temperature below the sticking point of said product.

In another aspect of this invention, the vibrating fluidized bed has at least one other fluidized bed connected therewith and the product from the vibrating fluidized bed is passed into said other bed to further increase the concentration of paraformaldehyde in the particles of said product by fluidizing said particles with an inert gas, said inert gas being at a temperature below the sticking point of the powder in said second bed and at a temperature greater than the temperature of the inert gas in said first bed. A hot, dry, free-flowing particulate paraformaldehyde is recovered from the last bed of said plurality of fluidized beds.

In yet another aspect of this invention, the product from the spray chamber may not be slightly sticky and agglomerated and may be simultaneously cured and dried in serially connected nonvibrating fluidized beds, later beds of said series operating at a temperature below the sticking point of the product in the bed and at a temperature higher than preceding beds.

In yet another aspect, this invention includes a process wherein the formaldehyde product removed from said spray chamber is slightly sticky and has many agglomerates, and is passed from said spray chamber into the first stage of a two-stage fluidized bed, the first stage being a vibratory fluidized bed which has an inert gas passing therethrough at a temperature of about 45°–75° C., and the second stage being optionally a vibratory fluidized bed which has an inert gas passing through it at a higher temperature in the range 70°–110° C.

BRIEF DESCRIPTION OF THE DRAWINGS

The accompany drawing diagrammatically shows an apparatus suitable for carrying out the process according to the invention.

DETAILED DESCRIPTION OF THE INVENTION

With reference to the drawing, heated formaldehyde solution having a concentration in the range of about 75 to about 90%, preferably about 84%, and heated to a temperature in the range 95°–140° C. is sprayed upwardly at a pressure of 6–7 atmospheres into spray chamber 1 through nozzle 2. The formaldehyde solution may contain the normal polymerization catalysts such as those described in U.S. Pat. No. 3,772,392, however, it is not necessary that catalysts be present. An inert cooling and drying gas, preferably nitrogen, is blown through said spray chamber in a downward direction by means of blower 3. Preferably the gas entering the spray chamber has a temperature less than about 50° C., preferably about 30°–40° C. Desirably the cooling and drying gas should have a temperature as low as possible to prevent excessive stickiness and reduce agglomerates in the product leaving the spray chamber, however, considerable cooling is not necessary since the process works well with gas having a temperature of about 30° to about 40° C. Desirably, the gas entering the spray chamber is not saturated with water and formaldehyde vapor when it contacts the liquid spray so that it has a drying action on the sprayed liquid.

Spray nozzle 2 is a standard nozzle giving a hollow cone spray pattern. Preferably nozzle diameters are in the range 0.7 to 2.5 millimeters. Such spray nozzles are commonly used in spray dryers for the drying of clay and ceramic materials. Spray cooling and drying chamber 1 may be equipped with electric or pneumatic knockers 4 and 4' which knock against the cone walls to dislodge sticky deposits of formaldehyde powder from the sides of the cone 4 and cause the deposits to slide towards cone outlet 5. A very small amount of product may become suspended in the cooling and drying gas and these are removed by cyclone 9 and passed to fluidized bed 6 discussed below. The cleaned gas is then passed through scrubber condenser 10 for further removal of formaldehyde and water vapor.

A solid product is continuously removed from cone outlet 5 and transferred into vibrating fluidized bed 6 which preferably has two stages 7 and 8. The product entering the first stage fluidized bed and leaving the spray chamber will usually be in the form of individual particles which are slightly sticky and lumped together into agglomerates which agglomerates have been found soft and not easy to handle. The temperature of the product entering the fluid bed is usually above 40° C. and most often between about 50° to about 60° C.

It is not altogether necessary that both stages 7 and 8 be vibrating fluidized beds. However, it is preferred that at least first stage 7 be a vibrating fluidized bed. A fluidizing gas such as nitrogen flows through the first stage bed at a temperature in the range 45°–75° C., preferably about 55° C. The sticky agglomerate mass does not fluidize immediately in the first fluidized bed. However, after about 10–20 minutes the product in the first stage fluidizes. Fluidization is continued for an additional 10–20 minutes.

While in the first stage of the fluidized bed, the product from the spray chamber simultaneously cures, loses some of its surface moisture, becomes nonsticky and is concentrated from its initial formaldehyde concentration of about 87% to a formaldehyde concentration of about 90%.

The product from the first fluidized bed 7 is transferred, preferably continuously, to a second stage of the fluidized bed which operates at a temperature higher than the first stage, preferably at a temperature in the range 70°–100° C. At the second stage fluidized bed the solid, dry particulate material is concentrated to a formaldehyde content of about 95%.

Fines blown out of the fluidized beds are passed to a cyclone 11 and then recycled into the final product. Gases emanating from the fluidized bed pass through cyclone 11 into a scrubber condenser 10 wherein water and formaldehyde are condensed and recycled to an evaporator for concentration of formaldehyde (not shown). The gases are then recycled to the spray cooling chamber 1. If needed, heater 12 may be activated to raise the temperature of the gases above the dewpoint.

It is within the contemplation of this invention that only a single unitary stage vibrating fluidized bed be used since for many purposes the product obtained from a single bed may have a satisfactory formaldehyde content. Further, it is possible to substitute a plurality of connected fluidized beds for the single multistage bed.

Whenever a plurality of fluidized beds or fluidized bed stages are used and the product emanating from the spray chamber is slightly sticky and agglomerated, at least the first bed should be a vibrating fluidized bed, the remaining fluidized beds or stages are desirably maintained at temperatures consecutively higher than the first bed. In the event three fluidized beds are used, the first may be run at a temperature in the range 45°–75° C., preferably 55° C., the second in the range 70°–100° C., preferably 75° C., and the third in the range 100°–125° C., preferably 110° C.

In the event the product emanating from the spray chamber is neither sticky nor agglomerated, it is not essential that a vibrating bed be used as the first fluidized bed, nevertheless the temperature of the fluidizing gas in the first bed should be maintained below the sticking point of the powder in the bed.

The preferred vibratory fluidized bed is standard commercial equipment of the type commonly used in processing spray dried milk powders. Typical of such equipment is the VIBRO-FLUIDIZER produced by NIRO ATOMIZER, INC. Fluidizing gas enters the bed at a velocity of 0.2 to 1.0 m/sec., preferably 0.2 to 0.4 m/sec.

The drying gas to the first stage of vibro-fluidizer comes from the scrubber condenser and is heated to 45°–75° C., preferably 55° C., prior to entering the material layer at 0.35 m/sec. After a period of about 10–20 minutes in the vibro-fluidizer the soft and somewhat sticky powder, which has a tendency for agglomeration and lump formation, is fluidized and consists mainly of the original formed prills. After a period of about ½ hour, the powder is transferred to the second stage of the vibro-fluidizer which operates with a gas inlet temperature of 75° C. A product of 94% by weight paraformaldehyde is then discharged at about 64° C. The product is free-flowing, substantially free of dust, and has a mean particle size in the range of from about 200 to 500 microns.

As part of the recovery process, it may be desirable to cool the hot discharged product. Cooling can readily be accomplished by transferring the discharged concentrated product to a fluidized cooling bed in which an inert gas having a temperature of about 30° C. is used as a fluidizing medium.

Although nitrogen has been mentioned as the preferred inert gas, other gases such as $CO_2$ may be used. Air can also be used but this increases the risk of explosion.

As indicated in the drawing the entire process is preferably run in continuous manner and in a closed cycle to eliminate escape of odor and obnoxious gases.

We claim:

1. A process for the production of a powdery, free-flowing paraformaldehyde comprising:
   a. forming a particulate formaldehyde product by spraying a concentrated aqueous formaldehyde solution containing from about 75% to about 90% formaldehyde by weight into a spray chamber and contacting the formaldehyde spray with an inert cooling gas flowing through said chamber,
   b. removing said particulate product from said spray chamber, said particulate product being at a temperature of from above 40° to about 60° C. and passing said product into the first of a plurality of fluidized beds,
   c. simultaneously drying, curing, and concentrating said product in said first bed by fluidizing said product with an inert gas, said gas being at a temperature below the sticking point of said product,
   d. passing the concentrated product from said first bed into at least one other fluidized bed connected therewith and further increasing the concentration of paraformaldehyde in the particles of said product by fluidizing said particles with a separate stream of inert gas, said separate inert gas being at a temperature below the sticking point of the powder in said other fluidized bed and at a temperature greater than the temperature of the inert gas in said first bed, and
   e. recovering a dry, free-flowing particulate paraformaldehyde from the last bed of said plurality of fluidized beds.

2. A process as claimed in claim 1 wherein said formaldehyde product entering said first fluidized bed has a formaldehyde concentration in the range 78–85% and said partially concentrated product leaving said first fluidized bed has a formaldehyde concentration in the range 85–91% formaldehyde and higher than that of the product entering said first fluidized bed.

3. A process as claimed in claim 1 wherein the inert gas in said first fluidized bed is at a temperature of from about 45° to 75° C.

4. A process as claimed in claim 3 wherein the inert gas in said other fluidized bed is at a temperature in the range 70° to about 100° C.

5. A process for the production of a powdery, free-flowing paraformaldehyde as claimed in claim 1 wherein said first fluidized bed is a vibrating fluidized bed.

6. A process as claimed in claim 5 wherein said product emanating from said spray chamber is slightly sticky and agglomerated.

7. A process as claimed in claim 5 wherein both said fluidized beds are vibrating beds.

8. A process as claimed in claim 7 wherein the process is conducted continuously and the inert gas entering said first fluidized vibrating bed is at a temperature in the range 45° to 75° C. and the inert gas entering said other fluidized vibrating bed is at a temperature in the range 70° to 100° C., and at higher temperature than that of the gas temperature in said first fluidized vibrating bed.

* * * * *